United States Patent [19]

Thompson et al.

[11] Patent Number: 5,777,214
[45] Date of Patent: Jul. 7, 1998

[54] IN-SITU CONTINUOUS WATER ANALYZING MODULE

[75] Inventors: Cyril V. Thompson, Knoxville; Marcus B. Wise, Kingston, both of Tenn.

[73] Assignee: Lockheed Martin Energy Research Corporation, Oak Ridge, Tenn.

[21] Appl. No.: 975,412

[22] Filed: Sep. 18, 1997

Related U.S. Application Data

[63] Continuation of Ser. No. 712,741, Sep. 12, 1996, abandoned.

[51] Int. Cl.[6] .............................. G01N 1/22; G01N 33/18
[52] U.S. Cl. ....................... 73/61.59; 73/19.12; 95/263; 96/202
[58] Field of Search .............................. 73/19.1, 19.12, 73/31.07, 61.59, 64.56, 863.21, 61.41, 61.43; 95/254, 263; 96/202

[56] References Cited

U.S. PATENT DOCUMENTS

| | | | |
|---|---|---|---|
| 3,800,595 | 4/1974 | Vincent | 73/19 |
| 3,942,792 | 3/1976 | Topol | 273/19 |
| 4,180,980 | 1/1980 | Marks et al. | 95/263 X |
| 4,613,347 | 9/1986 | Ranchet et al. | 96/202 X |
| 5,218,856 | 6/1993 | Doyle | 73/19.1 |
| 5,235,843 | 8/1993 | Langhorst | 73/19.02 |
| 5,272,337 | 12/1993 | Thompson et al. | 250/288 |
| 5,499,531 | 3/1996 | Henderson | 73/64.45 |

OTHER PUBLICATIONS

Gokhan Baykut and Ansette Voigt, "Spray Extraction of Volatile Organic Compounds from Aqueous Systems into the Gas Phase for Gas Chromatography/Mass Spectrometry," *Anal. Chem.*, 1992, 64, 677–681.

Scott J. Bauer and R. Graham Cooks, "MIMS for trace-level determination of organic analytes in on-line process monitoring and environmental analysis," *American Laboratory*, Oct. 1993, 36–51.

Primary Examiner—Michael Brock
Attorney, Agent, or Firm—Ivan L. Ericson

[57] ABSTRACT

An in-situ continuous liquid analyzing system for continuously analyzing volatile components contained in a water source comprises: a carrier gas supply, an extraction container and a mass spectrometer. The carrier gas supply continuously supplies the carrier gas to the extraction container and is mixed with a water sample that is continuously drawn into the extraction container. The carrier gas continuously extracts the volatile components out of the water sample. The water sample is returned to the water source after the volatile components are extracted from it. The extracted volatile components and the carrier gas are delivered continuously to the mass spectometer and the volatile components are continuously analyzed by the mass spectrometer.

21 Claims, 4 Drawing Sheets

5,777,214

1

IN-SITU CONTINUOUS WATER ANALYZING MODULE

This application is a continuation of application No. 08/712,741, filed Sep. 12, 1996, now abandoned.

This invention was made with Government support under contract DE-AC05-84OR21400 awarded by the U.S. Department of Energy to Lockheed Martin Energy Systems, Inc. and the Government has certain rights in this Invention.

FIELD OF THE INVENTION

The present invention relates to a water analyzing module, more particularly, to an in-situ continuous water analyzing module.

BACKGROUND OF THE INVENTION

Previous water analyses for volatile organic compounds have been performed by purge-and-trap gas chromatography/mass spectrometry or by direct sampling ion trap mass spectrometry by taking a representative aliquot of the water, typically 40 ml in a glass vial sealed with a Teflon-lined septum cap, and analyzing it by the requisite means. Analysis by purge-and-trap gas chromatography/ mass spectrometery took up to one hour per sample, while analysis by direct sampling ion trap mass spectrometry took around three minutes. Although the direct sampling ion trap mass spectrometry method was considerably faster, it still required that a sample be acquired from sites such as wells, surface water bodies, seeps, etc. Acquiring samples from wells generally involves purging three well volumes prior to taking the first sample for analysis. Both methods also require extensive paper work to maintain chain-of-custody record.

OBJECTS OF THE INVENTION

Accordingly, it is an object of the present invention to provide an in-situ continuous water analyzing module. Further and other objects of the present invention will become apparent from the description contained herein.

SUMMARY OF THE INVENTION

In accordance with one aspect of the present invention, a new and improved in-situ continuous liquid analyzing system for continuously analyzing volatile components of a liquid in a liquid source has a surface and a sampling depth. The in-situ continuous liquid monitoring system comprises: a carrier gas supply for continuously supplying a carrier gas, a carrier gas directing means, a first mass flow control means, a second mass flow control means, a sample gas delivering means, a sample gas analyzing means for continuously analyzing the volatile components contained in the liquid, an extraction container, a liquid directing means having a carrier gas inlet port, a liquid inlet port and a liquid outlet port and an extraction container depth positioning means having a cable attached thereto and attached to the extraction container. The extraction container, liquid directing means and carrier gas directing means can be made from any material which will withstand the environment they will be subjected to. One embodiment of the extraction container, liquid directing means and carrier gas directing means was made out of stainless steel. The extraction container has a carrier gas inlet port, a sample gas outlet port, a liquid outlet port and a support means for supporting the liquid directing means. The sample gas analyzing means has a sample gas inlet port. The extraction container has a first end and a

2 second end. The extraction container has a carrier gas inlet port and a sample gas outlet port at the first end and a liquid outlet port at the second end. The first mass flow control valve controls the flow of the carrier gas from the carrier gas supply means to the carrier gas directing means and the second mass flow control valve controls the flow of the sample gas from the extraction chamber to the sample gas analyzing means. The liquid outlet port at the second end of the extraction container is positioned parallel to and below the surface of the liquid source. The liquid directing means extends into the extraction container through the liquid outlet port of the extraction container and is supported by the support means of the extraction container. The liquid outlet port of the liquid directing means is positioned within the extraction container and the liquid inlet port of the liquid directing means is positioned outside the extraction container. The carrier gas supply is in communication with the first mass flow control means and the first mass flow control means is in communication with the carrier gas inlet port of the extraction container. The carrier gas directing means is in communication with and attached to the carrier gas inlet port. The carrier gas directing means has a carrier gas outlet port. The sample gas outlet port of the extraction container is in communication with the second mass flow control valve. The second mass flow control means is in communication with the sample gas delivering means. The sample gas delivering means is in communication with the sample gas inlet port of the gas analyzing means. The liquid directing means is in communication with and is supported by the support means of the extraction container.

In accordance with another aspect of the present invention, a new and improved method for continuously analyzing volatile components of a liquid in a liquid source comprises the following steps:

Step 1. An in-situ continuous liquid analyzing system is provided for continuously analyzing volatile components of a liquid in a liquid source having a surface and a sampling depth. The in-situ continuous liquid analyzing system comprises: a carrier gas supply for continuously supplying a carrier gas, a carrier gas directing means, a first mass flow control means, a second mass flow control means, a sample gas delivering means, a sample gas analyzing means for continuously analyzing the volatile components contained in the liquid, an extraction container, a liquid directing means having a carrier gas inlet port, a liquid inlet port and a liquid outlet port and an extraction container depth positioning means having a cable attached thereto and attached to the extraction container. The extraction container, liquid directing means and carrier gas directing means can be made from any material which will withstand the environment they will be subjected to or not react with the volatile components. One embodiment of the extraction container, liquid directing means and carrier gas directing means was made out of stainless steel. The extraction container has a carrier gas inlet port, a sample gas outlet port, a liquid outlet port and a support means for supporting the liquid directing means. The sample gas analyzing means has a sample gas inlet port. The extraction container has a first end and a second end. The extraction container has a carrier gas inlet port and a sample gas outlet port at the first end and a liquid outlet port at the second end. The first mass flow control means controls the flow of the carrier gas from the carrier gas supply means to the carrier gas directing means and the second mass flow control means controls the flow of the sample gas from the extraction chamber to the sample gas analyzing means. The liquid outlet port at the second end of the extraction container is positioned parallel to and below the surface of the liquid source. The liquid directing means extends into the extraction container through the liquid outlet port of the extraction container and is supported by the support means of the extraction container. The liquid outlet port of the liquid directing means is positioned within the extraction container and the liquid inlet port of the liquid directing means is positioned outside the extraction container. The carrier gas supply is in communication with the first mass control valve and the first mass flow control means is in communication with the carrier gas inlet port of the extraction container. The carrier gas directing means is in communication with and attached to the carrier gas inlet port. The carrier gas directing means has a carrier gas outlet port. The sample gas outlet port of the extraction container is in communication with the second mass flow control means. The second mass flow control means is in communication with the sample gas delivering means. The sample gas delivering means is in communication with the sample gas inlet port of the gas analyzing means. The liquid directing means is in communication with and is supported by the support means of the extraction container.

Step 2. The extraction container is positioned in the liquid source to be tested at a position where the liquid inlet port of the liquid directing means is positioned at the sample depth.

Step 3. The liquid is continuously drawn from the liquid source into the liquid inlet port and flowed through the liquid directing means and out of the liquid outlet port of the liquid directing means by the negative pressure created within the extraction container by the sample gas delivering means, thus refreshing the liquid from the source liquid inside the liquid directing means continually. The carrier gas contacts the liquid flowing within the liquid directing means for a period of time sufficient to extract the volatile components within the flowing liquid forming a sample gas. The sample gas containing the extracted volatile components of the liquid and the carrier gas exits the liquid outlet port of the liquid directing means into the extraction container and exits through the sample gas outlet port of the extraction container and is delivered into the sample gas inlet port of the sample gas analyzing means by the sample gas delivering means.

Step 5. The volatile components in the sample gas are continuously analyzed with the analyzing means.

In accordance with another aspect of the present invention, a new and improved in-situ continuous liquid analyzing system for continuously analyzing volatile components of a liquid in a liquid source has a surface and a sampling depth. The in-situ continuous liquid analyzing system comprises: a carrier gas supply means for continuously supplying carrier gas, a carrier gas directing means, a first mass flow control means, a second mass flow control means, a sample gas delivering means, a sample gas analyzing means, for continuously extracting the volatile components contained in the liquid, an extraction container, a liquid directing means which has a liquid inlet port and a liquid outlet port and an extraction container depth positioning means. The extraction container has a carrier gas inlet port, a sample gas outlet port, a liquid outlet port and a support means for supporting liquid directing means. The sample gas analyzing means has a sample gas inlet port. The extraction container has a first end and a second end. The extraction container has a carrier gas inlet port and a sample gas outlet port at the first end and a liquid outlet port at the second end. The first mass flow control means controls the flow of the carrier gas from the carrier gas supply means to the carrier gas directing means and the second mass flow control means controls the flow of the sample gas from the extraction chamber to the sample gas analyzing means. The liquid outlet port at the second end of the extraction container is positioned parallel to and below the surface of the liquid source. The liquid directing means extends into the extraction container through the liquid outlet port of the extraction container and is supported by the support means of the extraction container. The liquid outlet port of the liquid directing means is positioned within the extraction container and the liquid inlet port of the liquid directing means is positioned outside the extraction container. The liquid directing means positioned outside the extraction container is coiled to provide an extended length to the liquid directing means and maintaining a position relatively close to the extraction container. The carrier gas supply is in communication with the first mass flow control means and the first mass flow control means is in communication with the carrier gas inlet port of the extraction container. The carrier gas directing means is in communication with and attached to the carrier gas inlet port. The carrier gas directing means has a carrier gas outlet port. The carrier gas directing means has an upper portion and a lower portion. The lower portion of the carrier gas directing means is positioned within the liquid directing means. The upper portion of the carrier gas directing means is in communication with the carrier gas inlet port of the extraction container. The carrier gas outlet port is positioned within the liquid directing means and above the liquid inlet port of the liquid directing means. The lower portion of the carrier gas directing means has a length slightly shorter than the length of the liquid directing means to maintain the carrier gas outlet port above the liquid inlet port of the liquid directing means. The sample gas outlet port of the extraction container is in communication with the second mass flow control means. The second mass flow control means is in communication with the sample gas delivering means. The sample gas delivering means is in communication with the sample gas inlet port of the gas analyzing means. The liquid directing means is in communication with and supported by the support means of the extraction container.

In accordance with another aspect of the present invention a new and improved method for continuously analyzing volatile components of a liquid in a liquid source comprises the following steps:

Step 1. An in-situ continuous liquid analyzing system is provided for continuously analyzing volatile components of the liquid in the liquid source having a surface and a sampling depth. The in-situ continuous liquid analyzing system comprises: a carrier gas supply means for continuously supplying a carrier gas, a carrier gas directing means, a first mass flow control means, a second mass flow control means, a sample gas delivering means, a sample gas analyzing means, for continuously extracting the volatile components contained in the liquid, an extraction container, a liquid directing means which has a liquid inlet port and a liquid outlet port and an extraction container depth positioning means. The extraction container has a carrier gas inlet port, a sample gas outlet port, a liquid outlet port and a support means for supporting liquid directing means. The sample gas analyzing means has a sample gas inlet port. The extraction container has a first end and a second end. The extraction container has a carrier gas inlet port and a sample gas outlet port at the first end and a liquid outlet port at the second end. The first mass flow control means controls the flow of the carrier gas from the carrier gas supply means to the carrier gas directing means and the second mass flow control means controls the flow of the sample gas from the extraction chamber to the sample gas analyzing means. The liquid outlet port at the second end of the extraction container is positioned parallel to and below the surface of the liquid source. The liquid directing means extends into the extraction container through the liquid outlet port of the extraction container and is supported by the support means of the extraction container. The liquid outlet port of the liquid directing means is positioned within the extraction container and the liquid inlet port of the liquid directing means is positioned outside the extraction container. The liquid directing means positioned outside the extraction container is coiled to provide an extended length to the liquid directing means and maintaining a position relatively close to the extraction container. The carrier gas supply is in communication with the first mass flow control means and the first mass flow control means is in communication with the carrier gas inlet port of the extraction container. The carrier gas directing means is in communication with and attached to the carrier gas inlet port. The carrier gas directing means has a carrier gas outlet port. The carrier gas directing means has an upper portion and a lower portion. The lower portion of the carrier gas directing means is positioned within the liquid directing means. The upper portion of the carrier gas directing means is in communication with the carrier gas inlet port of the extraction container. The carrier gas outlet port is positioned within the liquid directing means and above the liquid inlet port of the liquid directing means. The lower portion of the carrier gas directing means has a length slightly shorter than the length of the liquid directing means to maintain the carrier gas outlet port above the liquid inlet port of the liquid directing means. The sample gas outlet port of the extraction container is in communication with the second mass flow control means. The second mass flow control means is in communication with the sample gas delivering means. The sample gas delivering means is in communication with the sample gas inlet port of the gas analyzing means. The liquid directing means is in communication with and supported by the support means of the extraction container.

Step 2. The extraction container is positioned in the liquid source to be tested by the extraction container depth positioning means at a position where the liquid inlet port of the liquid directing means is positioned at the sample depth.

Step 3. The liquid is continuously drawn from the liquid source into the liquid inlet port and flowed through the liquid directing means and out of the liquid outlet port of the liquid directing means by the sample gas delivering means and the carrier gas flowing into the liquid directing means through the carrier gas outlet port positioned within the liquid directing means by a negative pressure created within the extraction container by the sample gas delivering means, thus refreshing the liquid from the source liquid inside the liquid directing means continually. The carrier gas contacts the liquid flowing within the liquid directing means for a period of time sufficient to extract the volatile components from the liquid forming a sample gas. The sample gas containing the extracted volatile components of the liquid and the carrier gas exits the liquid outlet port of the liquid directing means into the extraction container and exits through the sample gas outlet port of the extraction container and is delivered into the sample gas inlet port of the sample gas analyzing means by the sample gas delivering means.

Step 5. The volatile components in the sample gas are continuously analyzed with the sample gas analyzing means.

For a better understanding of the present invention, together with other and further objects, advantages and capabilities thereof, reference is made to the following disclosure and appended claims in connection with the above described drawings.

DETAILED DESCRIPTION OF THE PREFERRED EMBODIMENTS

The present invention eliminates the requirement for actually acquiring a separate sample, as it operates on the water sample in-situ, wherever that might be. Analyses of volatile organic compounds in water can be performed on any water sample that the in-situ water monitor of the present invention can be deployed in, including deep water wells. Use of this device eliminates the sample acquisition, paperwork for chain-of-custody records, and disposal of the processed sample which are required for the previously mentioned methods. The sensitivity of the module of the present invention is comparable to that achievable with the soil/water purge module previously patented by the inventors in U.S. Pat. No. 5,272,337. It has been deployed twice in field tests with great success, with a monitoring rate for wells of about 4 per hour. It can also be deployed with devices such as cone penetrometers (via hydro-punch) or Geoprobes. An added benefit is that analytical results are available immediately in the field at the site of characterization or remediation, where they can be used to direct pertinent field operations such as well placement or groundwater treatment.

Figure 1:
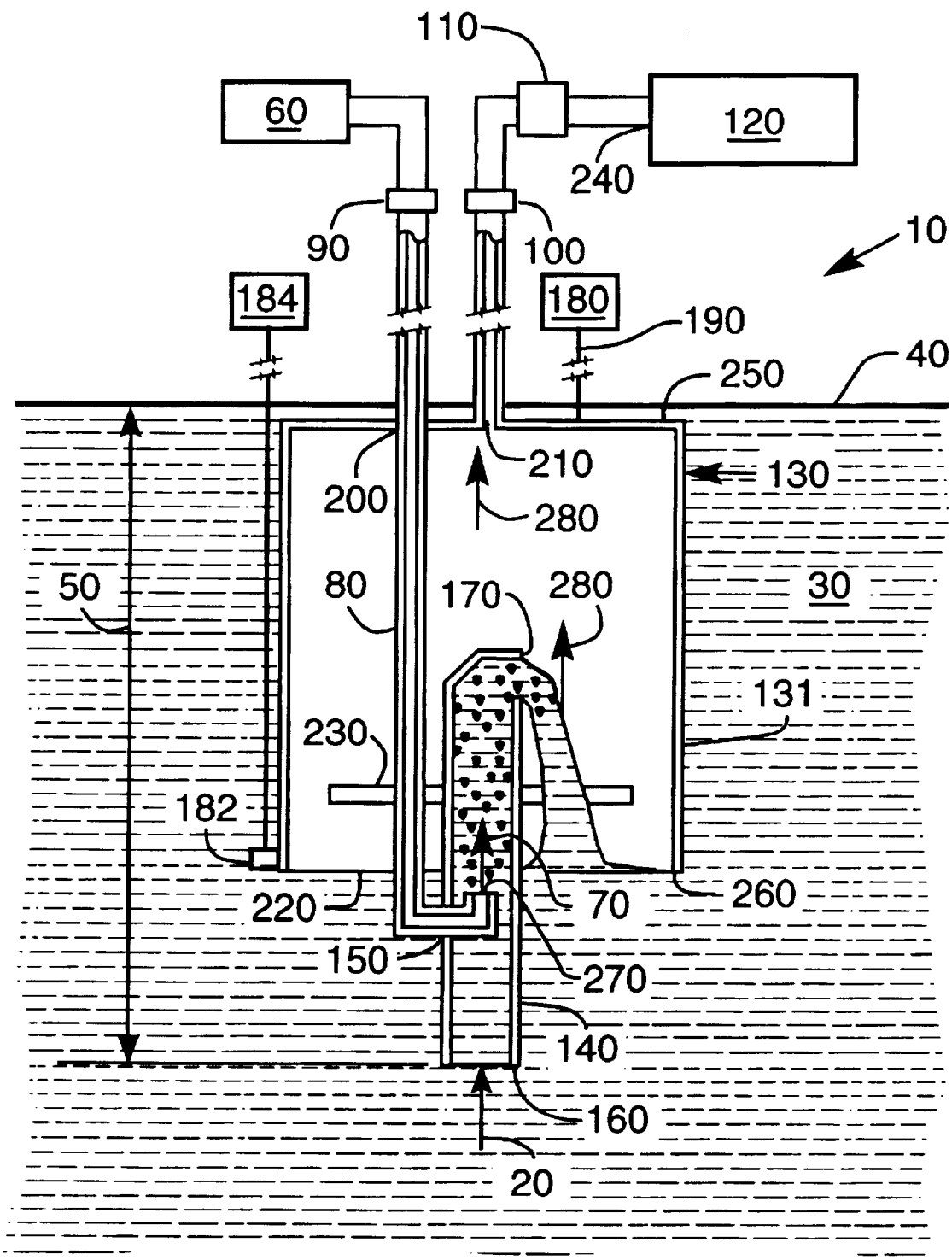
FIG. 1 is a cross-sectional view of an in-situ continuous liquid monitoring system in accordance with the present invention.

Shown in FIG. 1 is in-situ continuous liquid analyzing system 10 for continuously analyzing volatile components of liquid 20 in liquid source 30 having surface 40 and sampling depth 50. In-situ continuous liquid analyzing system 10 comprises: carrier gas supply means 60, such as a pressurized gas cylinder of helium having a pressure regulator and a mass flow controller attached thereto, for continuously supplying carrier gas 70, such as helium, carrier gas directing means 80, such as a tube, a first mass flow control means 90, a second mass flow control means 100, sample gas delivering means 110, such as a vacuum pump placed on the open/split interface of the mass spectrometer sample line, sample gas analyzing means 120, such as a mass spectrometer as described in U.S. Pat. No. 5,272,337 to Thompson et al incorporated herein by reference thereto, for continuously extracting the volatile components contained in liquid 20, extraction container 130, liquid directing means 140, such as a tube, having carrier gas inlet port 150, liquid inlet port 160 and liquid outlet port 170 and extraction container depth positioning means 180, such as a winch, having cable 190 attached thereto and attached to extraction container 130. Liquid level detection means 182 is positioned on outside surface 131 of extraction container 130 above liquid outlet port 220 of extraction container 30. Liquid level indicating means 184 is in communication with liquid level detection means 182 to indicate when liquid outlet port 220 is below surface 40 of liquid source 30. Extraction container 130, liquid directing means 140 and carrier gas directing means 80 can be made from any material which will withstand the environment it will be subjected to and not affect the volatile components. One embodiment of extraction container 130, liquid directing means 140 and carrier gas directing means 80 was made out of stainless steel. Extraction container 130 has carrier gas inlet port 200, sample gas outlet port 210, liquid outlet port 220 and support means 230 for supporting liquid directing means 140. Sample gas analyzing means 120 has sample gas inlet port 240. Extraction container 130 has first end 250 and second end 260. Extraction container 130 has carrier gas inlet port 200 and sample gas outlet port 210 at first end 250 and liquid outlet port 220 at second end 260. First mass control valve 90, such as a miniature mass flow controller, UFC-8260 made by UNIT Instruments, Inc. Yorba Linda, CA, controls the flow of carrier gas from carrier gas supply means 60 to carrier gas directing means 80 and second mass control valve 100, such as a miniature mass flow controller, UFC-8260 made by UNIT Instruments, Inc. Yorba Linda, CA, controls the flow of sample gas from extraction chamber 130 to sample gas analyzing means 120. Liquid outlet port 220 at second end 260 of extraction container 130 is positioned parallel to and below surface 40 of liquid source 30. Liquid directing means 140 extends into extraction container 130 through liquid outlet port 220 of extraction container 130 and is supported by support means 230 of extraction container 130. Liquid outlet port 170 of liquid directing means 140 is positioned within extraction container 130 and liquid inlet port 160 of liquid directing means 140 is positioned outside extraction container 130. Carrier gas supply 60 is in communication with first mass flow control means 90 and first mass flow control means 90 is in communication with carrier gas inlet port 200 of extraction container 130. Carrier gas directing means 80 is in communication with and attached to carrier gas inlet port 200. Carrier gas directing means 80 has carrier gas outlet port 270. Sample gas outlet port 210 of extraction container 130 is in communication with second mass flow control means 100. Second mass flow control means 100 is in communication with sample gas delivering means 110. Sample gas delivering means 110 is in communication with sample gas inlet port 240 of gas analyzing means 120. Liquid directing means 140 is in communication with and supported by support means 230 of extraction container 130.

The method for continuously analyzing volatile components of liquid 20 in liquid source 30 comprises the following steps:

Step 1. An in-situ continuous liquid analyzing system 10 is provided for continuously analyzing volatile components of liquid 20 in liquid source 30 having surface 40 and sampling depth 50. In-situ continuous liquid analyzing system 10 comprises: carrier gas supply means 60, for continuously supplying carrier gas 70, carrier gas directing means 80, a first mass flow control means 90, a second mass flow control means 100, sample gas delivering means 110, sample gas analyzing means 120 for continuously extracting the volatile components contained in liquid 20, extraction container 130, liquid directing means 140, having carrier gas inlet port 150, liquid inlet port 160 and liquid outlet port 170 and extraction container depth positioning means 180. Liquid level detection means 182 is positioned on outside surface 131 of extraction container 130 above liquid outlet port 220 of extraction container 30. Liquid level indicating means 184 is in communication with liquid level detection means 182 to indicate when liquid outlet port 220 is below surface 40 of liquid source 30. Extraction container 130 has carrier gas inlet port 200, sample gas outlet port 210, liquid outlet port 220 and support means 230 for supporting liquid directing means 140. Sample gas analyzing means 120 has sample gas inlet port 240. Extraction container 130 has first end 250 and second end 260. Extraction container 130 has carrier gas inlet port 200 and sample gas outlet port 210 at first end 250 and liquid outlet port 220 at second end 260. First mass flow control means 90 controls the flow of carrier gas from carrier gas supply means 60 to carrier gas directing means 80 and second mass flow control means 100, such as a miniature mass flow controller controls the flow of sample gas from extraction chamber 130 to sample gas analyzing means 120. Liquid outlet port 220 at second end 260 of extraction container 130 is positioned parallel to and below surface 40 of liquid source 30. Liquid directing means 140 extends into extraction container 130 through liquid outlet port 220 of extraction container 130 and is supported by support means 230 of extraction container 130. Liquid outlet port 170 of liquid directing means 140 is positioned within extraction container 130 and liquid inlet port 160 of liquid directing means 140 is positioned outside extraction container 130. Carrier gas supply 60 is in communication with first mass flow control means 90 and first mass flow control means 90 is in communication with carrier gas inlet port 200 of extraction container 130. Carrier gas directing means 80 is in communication with and attached to carrier gas inlet port 200. Carrier gas directing means 80 has carrier gas outlet port 270. Sample gas outlet port 210 of extraction container 130 is in communication with second mass flow control means 100. Second mass flow control means 100 is in communication with sample gas delivering means 110. Sample gas delivering means 110 is in communication with sample gas inlet port 240 of gas analyzing means 120. Liquid directing means 140 is in communication with and supported by support means 230 of extraction container 130.

Step 2. Extraction container 130 is positioned in liquid source 30 to be tested at a position where liquid inlet port 160 of liquid directing means 140 is positioned at sample depth 50 sufficient to position liquid level detection means 182 below surface 40 of liquid source 30.

Step 3. Liquid 20 is continuously drawn from liquid source 30 into liquid inlet port 160 and flowed through liquid directing means 140 and out of liquid outlet port 170 of liquid directing means 140 by sample gas delivering means 110 and carrier gas 70 flowing into liquid directing means 140 through carrier gas outlet port 270 positioned within liquid directing means by the negative pressure created within extraction container 130 by sample gas delivering means 110, thus refreshing liquid 20 from source liquid 30 inside liquid directing means 140 continually. Carrier gas 70 contacts liquid 20 flowing within liquid directing means 140 for a period of time sufficient to extract the volatile components within flowing liquid 20 forming a sample gas 280. Sample gas 280 containing the extracted volatile components of liquid 20 and carrier gas 70 exits liquid outlet port 170 of liquid directing means 140 into extraction container 130 and exits through sample gas outlet port 210 of extraction container 130 and is delivered into sample gas inlet port 240 of sample gas analyzing means 120 by sample gas delivering means.

Step 5. The volatile components in sample gas 280 are continuously analyzed with analyzing means 120.

Figure 2:
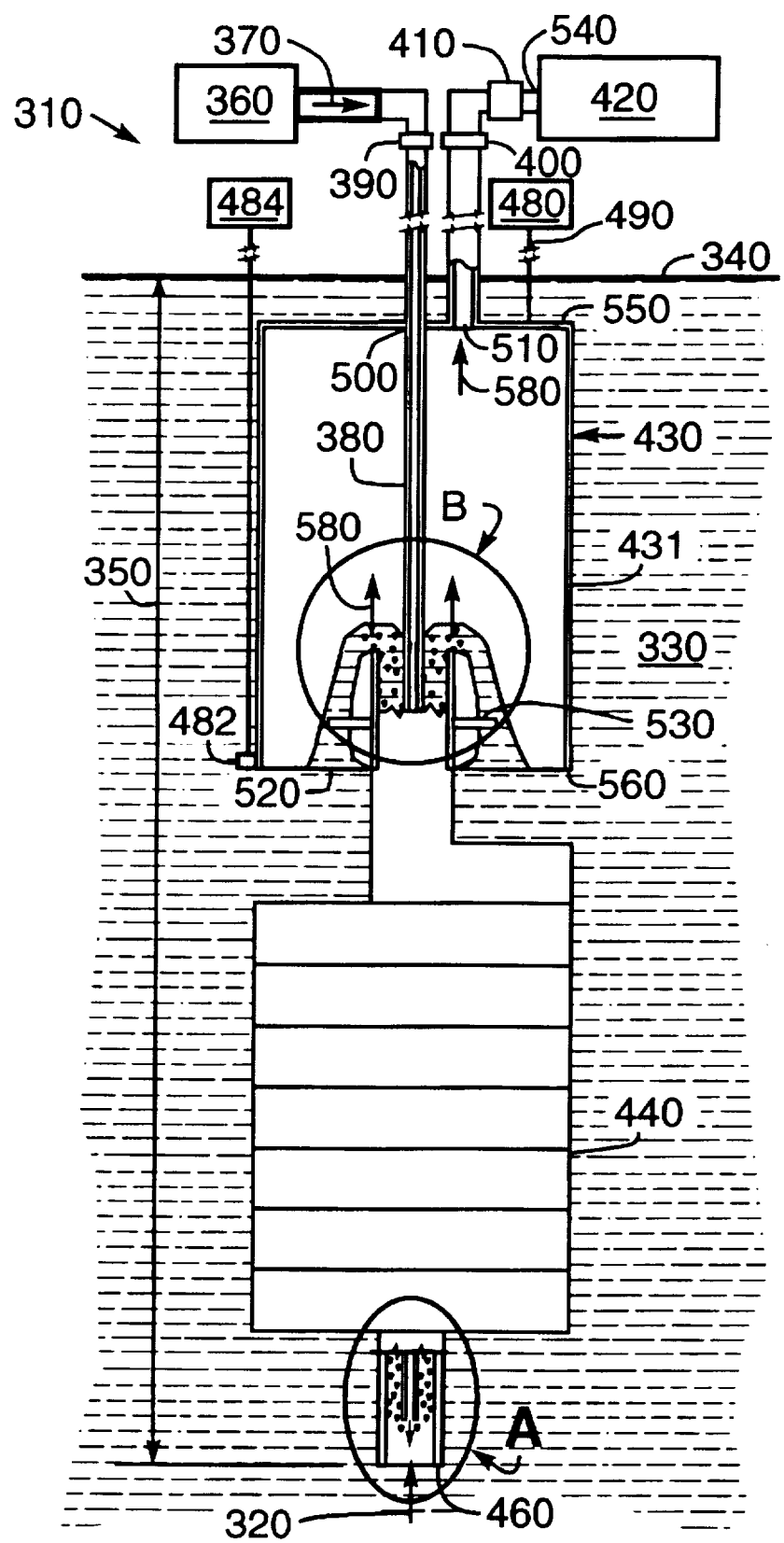
FIG. 2 is a cross-sectional view of an in-situ continuous liquid monitoring system in accordance with the present invention.
Figure 3:
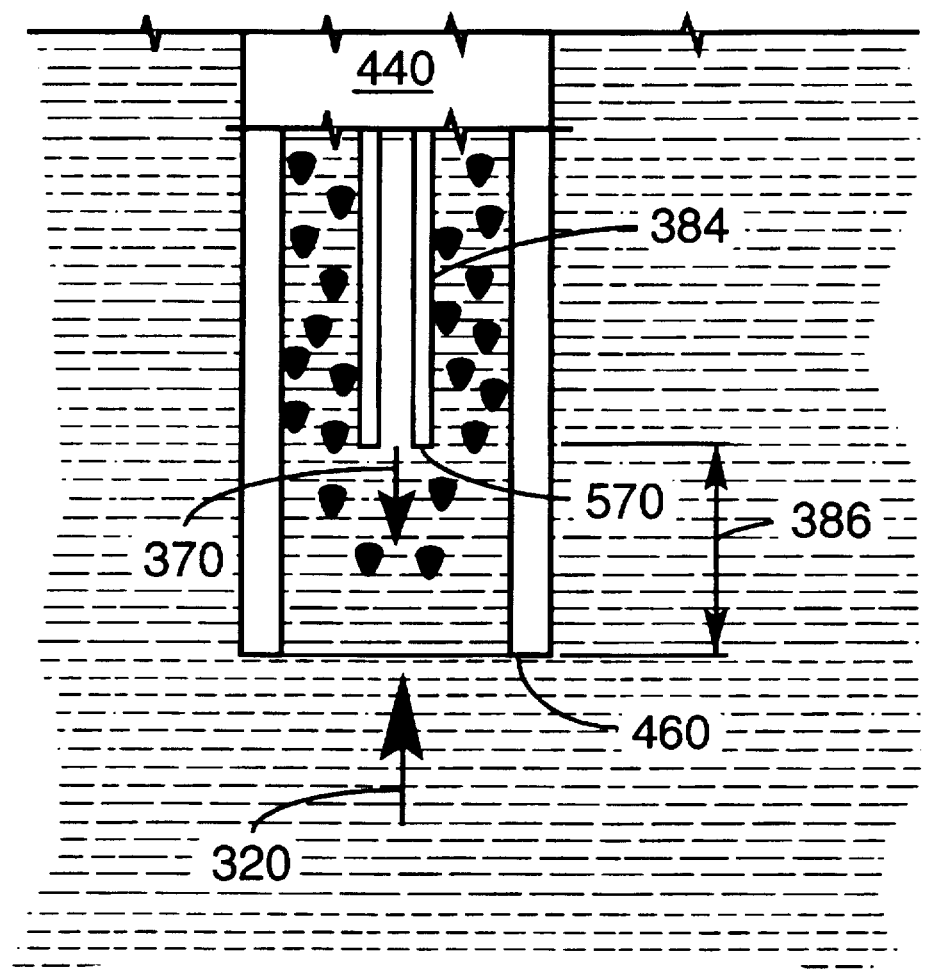
FIG. 3 is a magnified cross-sectional view of area A of FIG. 2 in accordance with the present invention.
Figure 4:
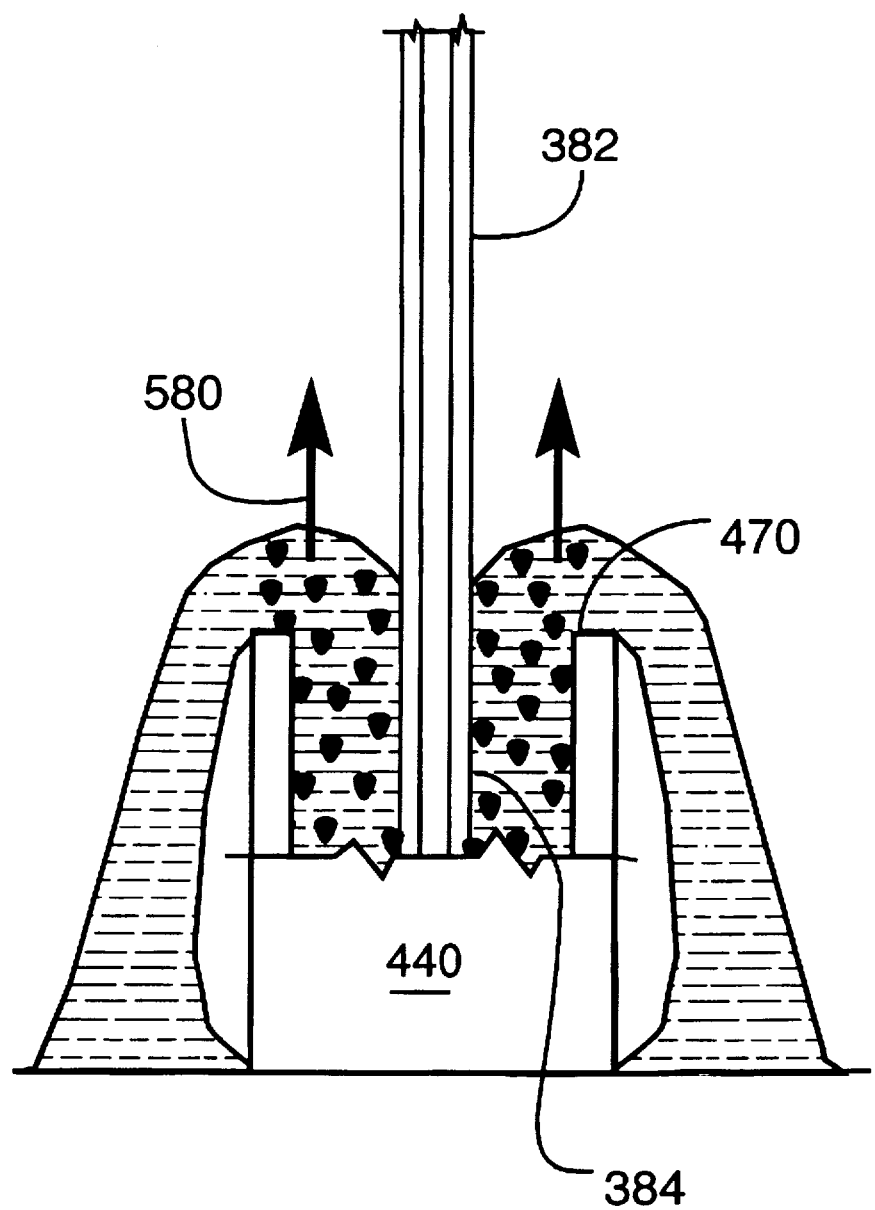
FIG. 4 is a magnified cross-sectional view of area B of FIG. 2 in accordance with the present invention.

Shown in FIG. 2 is in-situ continuous liquid analyzing system 310 for continuously analyzing volatile components of liquid 320 in liquid source 330 having surface 340 and sampling depth 350. In-situ continuous liquid analyzing system 310 comprises: carrier gas supply means 360, such as a pressurized gas cylinder of helium having a pressure regulator and a valved flow meter attached thereto, for continuously supplying carrier gas 370, such as helium. carrier gas directing means 380, such as a tube, first mass flow control means 390, such as a miniature mass flow controller, UFC-8260 made by UNIT Instruments, Inc. Yorba Linda, CA, for controlling a flow of carrier gas 370, second mass control valve 400, such as a miniature mass flow controller, UFC-8260 made by UNIT Instruments, Inc. Yorba Linda, CA, for controlling a flow of sample gas 580, sample gas delivering means 410, such as a vacuum pump placed on the open/split interface of the mass spectrometer sample line, sample gas analyzing means 420, such as a mass spectrometer as described in U.S. Pat. No. 5,272,337 to Thompson et al incorporated herein by reference thereto, for continuously extracting the volatile components contained in liquid 320, extraction container 430, liquid directing means 440, such as a tube, having liquid inlet port 460 and liquid outlet port 470 and extraction container depth positioning means 480, such as a winch, having cable 490 attached thereto and attached to extraction container 430. Liquid level detection means 482 is positioned on outside surface 431 of extraction container 430 above liquid outlet port 520 of extraction container 330. Liquid level indicating means 484 is in communication with liquid level detection means 482 to indicate when liquid outlet port 520 is below surface 340 of liquid source 330. Extraction container 430, liquid directing means 440 and carrier gas directing means 380 can be made from any material which will withstand the environment it will be subjected to and not affect the volatile components. One embodiment of extraction container 430, liquid directing means 440 and carrier gas directing means 380 was made out of stainless steel. Extraction container 430 has carrier gas inlet port 500, sample gas outlet port 510, liquid outlet port 520 and support means 530 for supporting liquid directing means 440. Sample gas analyzing means 420 has sample gas inlet port 540. Extraction container 430 has first end 550 and second end 560. Extraction container 430 has carrier gas inlet port 500 and sample gas outlet port 510 at first end 550 and liquid outlet port 520 at second end 560. First mass flow control means 390 controls the flow of carrier gas from carrier gas supply means 360 to carrier gas directing means 380 and second mass flow control means 400 controls the flow of sample gas from extraction chamber 430 to sample gas analyzing means 420. Liquid outlet port 520 at second end 560 of extraction container 430 is positioned parallel to and below surface 340 of liquid source 330. Liquid directing means 540 extends into extraction container 530 through liquid outlet port 520 of extraction container 430 and is supported by support means 530 of extraction container 430. Liquid outlet port 470 of liquid directing means 440 is positioned within extraction container 430 and liquid inlet port 460 of liquid directing means 440 is positioned outside extraction container 430. Liquid directing means 540 positioned outside extraction container 430 is coiled to provide an extended length to liquid directing means 540 and maintain a position relatively close to extraction container 430. Carrier gas supply 360 is in communication with first mass flow control means 390 and first mass flow control means 390 is in communication with carrier gas inlet port 500 of extraction container 430. Carrier gas directing means 380 is in communication with and attached to carrier gas inlet port 500. Carrier gas directing means 380 has carrier gas outlet port 570. Carrier gas directing means 380 has upper portion 382 and lower portion 384. Shown in FIGS. 2 and 3 lower portion 384 of carrier gas directing means 380 is positioned within liquid directing means 440. Shown in FIG. 4 upper portion 382 of carrier gas directing means 380 is in communication with carrier gas inlet port 500 of extraction container 430. Shown in FIGS. 2 and 3 carrier gas outlet port 570 is positioned within liquid directing means 440 and above liquid inlet port 320 of liquid directing means 440. Lower portion 384 of carrier gas directing means 380 has carrier gas outlet port 570 located distance 386 above liquid inlet port 460 of liquid directing means 440. Distance 386 is sufficient to prevent carrier gas 370 from exiting liquid inlet port 460. Sample gas outlet port 510 of extraction container 430 is in communication with second mass flow control means 400. Second mass flow control means 400 is in communication with sample gas delivering means 410. Sample gas delivering means 410 is in communication with sample gas inlet port 540 of gas analyzing means 420. Liquid directing means 430 is in communication with and supported by support means 530 of extraction container 430.

The method for continuously analyzing volatile components of liquid 320 in liquid source 330 comprises the following steps:

Step 1. An in-situ continuous liquid analyzing system 310 is provided for continuously analyzing volatile components of liquid 320 in liquid source 330 having surface 340 and sampling depth 350. In-situ continuous liquid analyzing system 310 comprises: carrier gas supply means 360 for continuously supplying carrier gas 370, carrier gas directing means 380, sample gas delivering means 410, sample gas analyzing means 420 for analyzing sample gas 580, first mass flow control means 390 for controlling a flow of carrier gas 370, second mass flow control means 400 for controlling a flow of sample gas 580, liquid directing means 440 having liquid inlet port 460 and liquid outlet port 470 and extraction container depth positioning means 480. Liquid level detection means 482 is positioned on outside surface 431 of extraction container 430 above liquid outlet port 520 of extraction container 330. Liquid level indicating means 484 is in communication with liquid level detection means 482 to indicate when liquid outlet port 520 is below surface 340 of liquid source 330. Extraction container 430 has carrier gas inlet port 500, sample gas outlet port 510, liquid outlet port 520 and support means 530 for supporting liquid directing means 440. Sample gas analyzing means 420 has sample gas inlet port 540. Extraction container 430 has first end 550 and second end 560. Extraction container 430 has carrier gas inlet port 500 and sample gas outlet port 510 at first end 550 and liquid outlet port 520 at second end 560. First mass flow control means 390 controls the flow of carrier gas from carrier gas supply means 360 to carrier gas directing means 380 and second mass flow control means 400 controls the flow of sample gas from extraction chamber 430 to sample gas analyzing means 420. Liquid outlet port 520 at second end 560 of extraction container 430 is positioned parallel to and below surface 340 of liquid source 330. Liquid directing means 540 extends into extraction container 530 through liquid outlet port 520 of extraction container 430 and is supported by support means 530 of extraction container 430. Liquid outlet port 470 of liquid directing means 440 is positioned within extraction container 430 and liquid inlet port 460 of liquid directing means 440 is positioned outside extraction container 430. Liquid directing means 540 positioned outside extraction container 430 is coiled to provide an extended length to liquid directing means 540 while maintaining a position relatively close to extraction container 430. Carrier gas supply 360 is in communication with first mass flow control means 390 and first mass flow control means 390 is in communication with carrier gas inlet port 500 of extraction container 430. Carrier gas directing means 380 is in communication with and attached to carrier gas inlet port 500. Carrier gas directing means 380 has carrier gas outlet port 570. Carrier gas directing means 380 has upper portion 382 and lower portion 384. Shown in FIGS. 2 and 4 lower portion 384 of carrier gas directing means 380 is positioned within liquid directing means 440. Shown in FIG. 4 upper portion 382 of carrier gas directing means 380 is in communication with carrier gas inlet port 500 of extraction container 430. Shown in FIGS. 2 and 3 carrier gas outlet port 570 is positioned within liquid directing means 440 and above liquid inlet port 320 of liquid directing means 440. Lower portion 384 of carrier gas directing means 380 has length 386 slightly shorter than length 442 of liquid directing means 440 to maintain carrier gas outlet port 570 above liquid inlet port 320 of liquid directing means 440. Sample gas outlet port 510 of extraction container 430 is in communication with second mass flow control means 400. Second mass flow control means 400 is in communication with sample gas delivering means 410. Sample gas delivering means 410 is in communication with sample gas inlet port 540 of gas analyzing means 420. Liquid directing means 430 is in communication with and supported by support means 530 of extraction container 430;

Step 2. Extraction container 430 is positioned in liquid source 330 to be tested by extraction container depth positioning means 480 at a position where liquid inlet port 460 of liquid directing means 440 is positioned at sample depth 350 sufficient to position liquid level detection means 482 below surface 340 of liquid source 330.

Step 3. Liquid 320 is continuously drawn from liquid source 330 into liquid inlet port 460 and flowed through liquid directing means 440 and out of liquid outlet port 470 of liquid directing means 440 by sample gas delivering means 410 and carrier gas 370 flowing into liquid directing means 440 through carrier gas outlet port 570 positioned within liquid directing means by a negative pressure created within extraction container 430 by sample gas delivering means 410, thus refreshing liquid 320 from source liquid 330 inside liquid directing means 440 continually. Carrier gas 370 contacts liquid 320 flowing within liquid directing means 440 for a period of time sufficient to extract the volatile components from liquid 320 forming a sample gas 580. Sample gas 580 containing the extracted volatile components of liquid 320 and carrier gas 370 exits liquid outlet port 470 of liquid directing means 440 into extraction container 430 and exits through sample gas outlet port 510 of extraction container 430 and is delivered into sample gas inlet port 540 of sample gas analyzing means 420 by sample gas delivering means.

Step 5. The volatile components in sample gas 580 are continuously analyzed with analyzing means 420.

A method for use of the in situ water monitor of the present invention assumes the use of an analytical instrument, such as a mass spectrometer, capable of analyzing the effluent from the in situ water monitor in a continuous manner. The instrument should be equipped with a sampling interface such as the direct sampling interface, for optimum operation.

The in situ water monitor is connected to an umbilical of sufficient length to allow deployment to the maximum depth of the water to be sampled. The other end of the umbilical is connected to two mass flow controllers—one of which is used to control the flow of carrier gas down to the in situ water monitor and the other of which is used to control return flow from the in situ water monitor. The mass flow controllers are set to generate a slight (1 to 5 ml/min) excess of carrier gas flow to the in situ water monitor. The carrier gas supply is set to an operating pressure greater than the head pressure which will be exerted on the in situ water monitor by the water to be sampled. (The head pressure generated by water is 0.426 psi/foot.) For example, if the in situ water monitor is to be deployed to a water depth of 150 ft., the water pressure will be about 64 psi, and the carrier gas operating pressure should be set to about 80 psi. The flow rates of the carrier and return gases should be set such that the response time from sample uptake in the in situ water monitor to response at the instrument at the other end of the umbilical is not overly long. This response time may be determined either by sampling a standard at the surface or by injecting an inert gas such as Argon into the carrier gas stream and measuring the elapsed time to instrument response and dividing that time by two. The return gas from the umbilical is directed first into the transfer line interface on the mass spectrometer and through the archive port on the transfer line to the mass flow controller. The return gas flow is drawn through this arrangement by a vacuum pump on the downstream side of the mass flow controller.

The in situ water monitor may be calibrated with external standards (i.e. standards in a beaker) prior to or after completion of water sampling. For sampling, the in situ water monitor may be lowered very gradually, in a continuous manner into the water to be sampled, thus generating a continuous profile of analyte concentration as a function of depth. The water may also be profiled by incrementally lowering the in situ water monitor to discrete depths and sampling for set periods of time. Concentrations of volatile organic compounds in the sampled water may be determined by comparison with the calibration curve generated from the external standard calibration.

A particular advantage of this invention is the ability to sample the liquid from different depths of the liquid source being analyzed. This is accomplished by lowering the extraction container to a depth whereby the liquid inlet port is at the sampling depth.

The extraction container, liquid directing means and carrier gas directing means of the present invention require no moving parts, no electrical power, and can be deployed in very small spaces.

Varying versions of this invention can be designed for and permanently deployed in wells at very little cost, permitting in-situ sampling of the wells and eliminating costly bailing/pumping of the well for sample acquisition. Versions could be developed which would be adapted for use with ground penetrating probes as mentioned above.

This system could be used for field characterization of volatile organic compounds in water at suspected hazardous waste sites, for remediation monitoring of confirmed sites, for spot sampling of surface water to track chemical plumes, and for quick characterization of volatile organic compounds in any surface water. The demand for this system should greatly exceed that of the previous soil/water purge module due to its great flexibility of deployment. Both government and industry have considerable need for the capability provided by this invention.

The present invention provides for the immediate quantitation of volatile organic compounds in water. It also provides for the real-time monitoring of such compounds in water samples or process streams. Variations in the concentrations of these compounds can be detected and plotted in real-time. The present invention has been used successfully to monitor the volatiles levels water. The concentrations of a number of volatile organic compounds, such as toluene benzene, methyl ethyl ketone, TCA, DCA, xylenes, ethyl benzene and C2-Benzenes, were continuously followed during the treatment process for destroying the compounds.

One advantage of the present invention is that no water samples need be transferred, treated and then disposed of, especially if the samples are classified as a hazardous waste, a significant benefit over other methods of water analysis.

The present invention provides a device which can be completely submerged to conduct depth profiling of volatile organic compounds contained in a body of water. The mass flow controllers, operating in parallel, maintain both the carrier gas and the return sample gas flows, and the head pressure in the submerged extraction container. The head pressure, as well as a slight positive carrier gas flow, must be maintained in the extraction container to prevent water from being entrained in the sample gas umbilical line going to the sample gas analyzer and entering the analyzer. The coiled liquid directing means at the bottom of the extraction container is used to increase the contact between the helium carrier gas and the water being sampled. This should increase the response of the analyzer to the analytes, by increasing the concentration of analytes in the sample gas.

A typical experimental setup is the deployment of the extraction container at the end of two 150 foot sections of umbilical tubing, one containing the carrier gas going to the carrier gas directing means in the extraction container and the other delivering the sample gas from the extraction container to the mass spectrometer. The mass flow controllers are set (100 ml/min carrier gas and 99 ml/min return) to maintain head pressure in the extraction container and to ensure that there is a slight excess of sample gas containing the helium carrier gas and extracted volatile components in the extraction container to prevent water from entering the sample gas return tubing going to the mass spectrometer. The carrier gas supply pressure into the mass flow controller is set to exceed any head pressure which might be encountered in the extraction container. The return flow through the mass flow controller is maintained by the sample gas delivering means, a vacuum pump placed on the open\split interface on the mass spectrometer sample line. This maintains the sample flow to the mass spectrometer in a continuous manner.

The umbilical for the incoming carrier gas to the extraction container consists of carrier gas tubing (TFE, 1/16" OD, 1/32"ID) and the sample gas return tubing (TFE, 1/8"OD-1/16"ID or stainless steel, 1/16"od-0.040"id). The size of the carrier gas tubing is small to maintain a low profile umbilical. The size of the sample gas return tubing is small to lower the dead volume of the return tubing and to minimize the delay in response time from the point in time at which the water enters the extraction container to the point at which an analytical response is seen in the analyzer.

The present arrangement of this in-situ continuous liquid analyzing system also permits the system to be independently monitored by spiking the carrier gas stream with an aliquot of an inert gas, such as argon, to confirm proper operation of the mass spectrometer and to determine the response time of the system.

An example of a depth profile of $CCl_4$, TCE, and PCE contaminates found in a water well is shown in Table 1.

TABLE I

DEPTH PROFILE OF A WATER WELL

| Water depth (feet) | $CCl_4$ (ng/ml) | TCE (ng/ml) | PCE (ng/ml) |
|---|---|---|---|
| 20 | 237 | 401 | 327 |

TABLE I-continued

DEPTH PROFILE OF A WATER WELL

| Water depth (feet) | $CCl_4$ (ng/ml) | TCE (ng/ml) | PCE (ng/ml) |
|---|---|---|---|
| 40 | 219 | 431 | 269 |
| 60 | 253 | 327 | 226 |
| 70 | 499 | 253 | 187 |
| 75 | 311 | 294 | 167 |
| 80 | 390 | 334 | 151 |
| 95 | 325 | 261 | 124 |
| 100 | 320 | 216 | 115 |
| 105 | 365 | 168 | 105 |
| 110 | 372 | 169 | 106 |
| 114 | 403 | 171 | 111 |
| 116 | 408 | 176 | 110 |
| 118 | 574 | 187 | 100 |
| 120 | 973 | 202 | 117 |
| 121 | 2073 | 287 | 152 |

Table 1 depth profile of a contaminated water well utilizing the in situ water monitor of the present invention illustrates how the location of a contaminate such as $CCl_4$ and its concentration can be determined within a water well.

While there has been shown and described what is at present considered the preferred embodiments of the invention, it will be obvious to those skilled in the art that various changes and modifications may be made therein without departing from the scope of the invention as defined by the appended claims.

What is claimed is:

1. An in-situ continuous liquid analyzing system for continuously analyzing volatile components of a liquid in a liquid source having a surface and a sampling depth comprising: a carrier gas supply for continuously supplying a carrier gas, a carrier gas directing means, a first mass flow control means, a second mass flow control means, a sample gas delivering means, a mass spectrometer for continuously analyzing said volatile components contained in said liquid, an extraction container, a liquid directing means having a carrier gas inlet port, a liquid inlet port and a liquid outlet port and an extraction container depth positioning means, said extraction container having a carrier gas inlet port, a sample gas outlet port, a liquid outlet port and a support means for supporting said liquid directing means, said mass spectrometer having a sample gas inlet port, said extraction container having a first end and a second end, said carrier gas inlet port and said sample gas outlet port of said extraction container being located at said first end of said extraction container and said liquid outlet port of said extraction container being located at said second end of said extraction container, said first mass flow control means controls the flow of said carrier gas from said carrier gas supply means to said carrier gas directing means and said second mass flow control means controls the flow of said sample gas from said extraction chamber to said mass spectrometer, said liquid outlet port at said second end of said extraction container being positioned parallel to and below said surface of said liquid source, said liquid directing means extends into said extraction container through said liquid outlet port of said extraction container and being supported by said support means of said extraction container, said liquid outlet port of said liquid directing means being positioned within said extraction container and said liquid inlet port of said liquid directing means being positioned outside said extraction container, said carrier gas supply being in communication with said first mass flow control valve, said first mass flow control means being in communication with said carrier gas inlet port of said extraction container, said carrier gas directing means being in communication with and attached to said carrier gas inlet port, said carrier gas directing means having a carrier gas outlet port, said sample gas outlet port of said extraction container being in communication with said second mass flow control means, said second mass flow control means being in communication with said sample gas delivering means, said sample gas delivering means being in communication with said sample gas inlet port of said gas analyzing means, said liquid directing means being connected to and being supported by said support means of said extraction container, said first and second mass flow control means being miniature mass flow controllers and said extraction container further containing a liquid level detection means, in communication with a liquid level indicating means, positioned on an outside surface of said extraction container.

2. An in-situ continuous liquid analyzing system in accordance with claim 1 wherein said liquid is water.

3. An in-situ continuous liquid analyzing system in accordance with claim 1 wherein said carrier gas is helium.

4. An in-situ continuous liquid analyzing system in accordance with claim 1 wherein said carrier gas supply means is a pressurized gas cylinder of helium having a pressure regulator.

5. An in-situ continuous liquid analyzing system in accordance with claim 1 wherein said liquid directing means is tubing.

6. An in-situ continuous liquid analyzing system in accordance with claim 1 wherein said carrier gas directing means is tubing.

7. An in-situ continuous liquid analyzing system in accordance with claim 1 wherein said sample gas delivering means is a vacuum pump.

8. An in-situ continuous liquid analyzing system in accordance with claim 1 wherein said extraction container depth positioning means is a winch.

9. A method for continuously analyzing volatile components of a liquid in a liquid source comprising the following steps:

Step 1. providing an in-situ continuous liquid analyzing system for continuously analyzing volatile components of a liquid in a liquid source having a surface and a sampling depth comprising: a carrier gas supply for continuously supplying a carrier gas, a carrier gas directing means, a first mass flow control means, a second mass flow control means, a sample gas delivering means, a mass spectrometer for continuously analyzing said volatile components contained in said liquid, an extraction container, a liquid directing means having a carrier gas inlet port, a liquid inlet port and a liquid outlet port and an extraction container depth positioning means, said extraction container having a carrier gas inlet port, a sample gas outlet port, a liquid outlet port and a support means for supporting said liquid directing means, said mass spectrometer having a sample gas inlet port, said extraction container having a first end and a second end, said carrier gas inlet port and said sample gas outlet port of said extraction container being located at said first end of said extraction container and said liquid outlet port of said extraction container being located at said second end of said extraction container, said first mass flow control means controls the flow of said carrier gas from said carrier gas supply means to said carrier gas directing means and said second mass flow control means controls the flow of said sample gas from said extraction chamber to said mass spectrometer, said liquid outlet port at said second end of said extraction container being positioned parallel to and below said surface of said liquid source, said liquid directing means extends into said extraction container through said liquid outlet port of said extraction container and being supported by said support means of said extraction container, said liquid outlet port of said liquid directing means being positioned within said extraction container and said liquid inlet port of said liquid directing means being positioned outside said extraction container, said carrier gas supply being in communication with said first mass flow control means, said first mass flow control valve being in communication said carrier gas inlet port of said extraction container, said carrier gas directing means being in communication with and attached to said carrier gas inlet port, said carrier gas directing means having a carrier gas outlet port, said sample gas outlet port of said extraction container being in communication with said second mass flow control valve, said second mass flow control means being in communication with said sample gas delivering means, said sample gas delivering means being in communication with said sample gas inlet port of said gas analyzing means, said liquid directing means being connected to and being supported by said support means of said extraction container, said first and second mass flow control means being miniature mass flow controllers and said extraction container further containing a liquid level detection means, in communication with a liquid level indicating means, positioned on an outside surface of said extraction container;

Step 2. positioning said extraction container in said liquid source to be tested at a position where said liquid inlet port of said liquid directing means is positioned at said sample depth;

Step 3. continuously drawing said liquid from said liquid source into said liquid inlet port and flowing said liquid through said liquid directing means and out of said liquid outlet port of said liquid directing means by a negative pressure created within said extraction container by said sample gas delivering means, thus refreshing said liquid from said source liquid inside said liquid directing means continually, contacting said carrier gas with said liquid flowing within said liquid directing means for a period of time sufficient to extract said volatile components within said flowing liquid forming a sample gas, said sample gas containing said extracted volatile components of said liquid and said carrier gas exits said liquid outlet port of said liquid directing means into said extraction container and exits through said sample gas outlet port of said extraction container and being delivered into said sample gas inlet port of said mass spectrometer by said sample gas delivering means; and Step 4. continuously analyzing said volatile components in said sample gas with said analyzing means.

10. An in-situ continuous liquid analyzing system for continuously analyzing volatile components of a liquid in a liquid source having a surface and a sampling depth comprising: a carrier gas supply means for continuously supplying a carrier gas, a carrier gas directing means, a sample gas delivering means, a sample gas analyzing means for analyzing a sample gas, a first mass flow control means for controlling a flow of said carrier gas, a second mass flow control means for controlling a flow of said sample gas, an extraction container for continuously extracting said volatile components contained in said liquid, a liquid directing means having a liquid inlet port and a liquid outlet port and an extraction container depth positioning means, said extraction container having a carrier gas inlet port, a sample gas outlet port, a liquid outlet port and a support means for supporting liquid directing means, said sample gas analyzing means having a sample gas inlet port, said extraction container having a first end and a second end, said carrier gas inlet port and said sample gas outlet port of said extraction container being located at said first end of said extraction container and said liquid outlet port of said extraction container being located at said second end of said extraction container, said first mass flow control means controlling said flow of said carrier gas from said carrier gas supply means to said carrier gas directing means and said second mass flow control means controls said flow of said sample gas from said extraction chamber to said sample gas analyzing means, said liquid outlet port at said second end of said extraction container being positioned parallel to and below said surface of said liquid source, said liquid directing means extends into said extraction container through said liquid outlet port of said extraction container and being supported by said support means of said extraction container, said liquid outlet port of said liquid directing means being positioned within said extraction container and said liquid inlet port of said liquid directing means being positioned outside said extraction container, said liquid directing means being coiled and positioned outside said extraction container to provide an extended length to said liquid directing means and maintaining a position relatively close to said extraction container, said carrier gas supply being in communication with said first mass flow control means and said first mass flow control means being in communication with said carrier gas inlet port of said extraction container, said carrier gas directing means being in communication with and attached to said carrier gas inlet port, said carrier gas directing means having a carrier gas outlet port, said carrier gas directing means having an upper portion and a lower portion, said lower portion of said carrier gas directing means being positioned within said liquid directing means, said upper portion of said carrier gas directing means being in communication with said carrier gas inlet port of said extraction container, said carrier gas outlet port being positioned within said liquid directing means and above said liquid inlet port of said liquid directing means, said lower portion of said carrier gas directing means having a length slightly shorter than said length of said liquid directing means to maintain said carrier gas outlet port above said liquid inlet port of said liquid directing means, said sample gas outlet port of said extraction container being in communication with said second mass flow control means, said second mass flow control means being in communication with said sample gas delivering means, said sample gas delivering means being in communication with said sample gas inlet port of said gas analyzing means, said liquid directing means being connected to and supported by said support means of said extraction container.

11. An in-situ continuous liquid analyzing system in accordance with claim 10 wherein said liquid is water.

12. An in-situ continuous liquid analyzing system in accordance with claim 10 wherein said carrier gas is helium.

13. An in-situ continuous liquid analyzing system in accordance with claim 10 wherein said carrier gas supply means is a pressurized gas cylinder of helium having a pressure regulator.

14. An in-situ continuous liquid analyzing system in accordance with claim 10 wherein said sample gas analyzing means is a mass spectrometer.

15. An in-situ continuous liquid analyzing system in accordance with claim 10 wherein said first and second mass flow control means are miniature mass flow controllers.

16. An in-situ continuous liquid analyzing system in accordance with claim 10 wherein said liquid directing means is tubing.

17. An in-situ continuous liquid analyzing system in accordance with claim 10 wherein said carrier gas directing means is tubing.

18. An in-situ continuous liquid analyzing system in accordance with claim 10 wherein said sample gas delivering means is a vacuum pump.

19. An in-situ continuous liquid analyzing system in accordance with claim 10 wherein said extraction container depth positioning means is a winch.

20. An in-situ continuous liquid analyzing system in accordance with claim 10 which further contains a liquid level detection means in communication with a liquid level indicating means positioned on an outside surface of said extraction container.

21. A method for continuously analyzing volatile components of a liquid in a liquid source comprising the following steps:

Step 1. providing an in-situ continuous liquid analyzing system for continuously analyzing volatile components of a liquid in a liquid source having a surface and a sampling depth comprising: a carrier gas supply means for continuously a supplying carrier gas, a carrier gas directing means, a sample gas delivering means, a sample gas analyzing means for analyzing a sample gas, a first mass flow control means for controlling a flow of said carrier gas, a second mass flow control means for controlling a flow of said sample gas, an extraction container for continuously extracting said volatile components contained in said liquid, a liquid directing means having a liquid inlet port and a liquid outlet port and an extraction container depth positioning means, said extraction container having a carrier gas inlet port, a sample gas outlet port, a liquid outlet port and a support means for supporting liquid directing means, said sample gas analyzing means having a sample gas inlet port, said extraction container having a first end and a second end, said carrier gas inlet port and said sample gas outlet port of said extraction container being located at said first end of said extraction container and liquid outlet port of said extraction container being located at said second end of said extraction container, said first mass flow control means controlling said flow of said carrier gas from said carrier gas supply means to said carrier gas directing means and said second mass flow control means controls said flow of said sample gas from said extraction chamber to said sample gas analyzing means, said liquid outlet port at said second end of said extraction container being positioned parallel to and below said surface of said liquid source, said liquid directing means extends into said extraction container through said liquid outlet port of said extraction container and being supported by said support means of said extraction container, said liquid outlet port of said liquid directing means being positioned within said extraction container and said liquid inlet port of said liquid directing means being positioned outside said extraction container, said liquid directing means being coiled and positioned outside said extraction container to provide an extended length to said liquid directing means and maintaining a position relatively dose to said extraction container, said carrier gas supply being in communication with said first mass flow control means and said first mass flow control means being in communication with said carrier gas inlet port of said extraction container, said carrier gas directing means being in communication with and attached to said carrier gas inlet port, said carrier gas directing means having a carrier gas outlet port, said carrier gas directing means having an upper portion and a lower portion, said lower portion of said carrier gas directing means being positioned within said liquid directing means, said upper portion of said carrier gas directing means being in communication with said carrier gas inlet port of said extraction container, said carrier gas outlet port being positioned within said liquid directing means and above said liquid inlet port of said liquid directing means, said lower portion of said carrier gas directing means having a length slightly shorter than said length of said liquid directing means to maintain said carrier gas outlet port above said liquid inlet port of said liquid directing means, said sample gas outlet port of said extraction container being in communication with said second mass flow control means, said second mass flow control means being in communication with said sample gas delivering means, said sample gas delivering means being in communication with said sample gas inlet port of said gas analyzing means, said liquid directing means being connected to and supported by said support means of said extraction container;

Step 2. positioning said extraction container in said liquid source to be tested by said extraction container depth positioning means at a position where said liquid inlet port of the liquid directing means is positioned at said sample depth.

Step 3. continuously drawing said liquid from said liquid source into said liquid inlet port and flowing said liquid through said liquid directing means and out of said liquid outlet port of said liquid directing means by said sample gas delivering means and said carrier gas flowing into said liquid directing means through said carrier gas outlet port positioned within said liquid directing means by a negative pressure created within said extraction container by said sample gas delivering means, thus refreshing said liquid from said source liquid inside said liquid directing means continually, said carrier gas contacting said liquid flowing within said liquid directing means for a period of time sufficient to extract said volatile components from said liquid forming a sample gas, said sample gas containing said extracted volatile components of said liquid and said carrier gas exiting said liquid outlet port of said liquid directing means into said extraction container and exiting through said sample gas outlet port of said extraction container and being delivered into said sample gas inlet port of said sample gas analyzing means by said sample gas delivering means; and Step 4. continuously analyzing said volatile components in said sample gas with said sample gas analyzing means.

\* \* \* \* \*